United States Patent

Howells et al.

[11] Patent Number: 5,850,144
[45] Date of Patent: Dec. 15, 1998

[54] METHOD FOR DETECTING LEAKS IN A MEMBRANE

[75] Inventors: Harvey Howells, Richardson, Tex.; Guillermo M. Torres, Henderson, Nev.

[73] Assignee: Serrot Corporation, Henderson, Nev.

[21] Appl. No.: 923,068

[22] Filed: Sep. 3, 1997

[51] Int. Cl.$^6$ .......................... G01N 27/00; G01R 31/12; B65G 5/00
[52] U.S. Cl. ...................... 324/559; 324/557; 324/71.1; 340/605; 405/54
[58] Field of Search ....................... 324/557, 559, 324/515, 517, 527, 555, 556, 71.1; 340/604, 605; 405/53, 54, 108

[56] References Cited

U.S. PATENT DOCUMENTS

| | | | |
|---|---|---|---|
| 3,249,862 | 5/1966 | Mack et al. ............................. | 324/559 |
| 3,252,155 | 5/1966 | Surtees et al. ......................... | 340/242 |
| 4,184,786 | 1/1980 | Richards ................................ | 405/108 |
| 4,914,395 | 4/1990 | Hamada ................................. | 324/557 |
| 5,084,680 | 1/1992 | Mitchell et al. ....................... | 324/559 |
| 5,288,168 | 2/1994 | Spencer ................................. | 340/605 |

*Primary Examiner*—Diep N. Do
*Attorney, Agent, or Firm*—Klein & Szekeres, LLP

[57] ABSTRACT

A leak-testable, fluid-impervious membrane is formed as a laminate of a conductive mesh scrim between upper and lower insulative polymeric resin layers. The scrim is preferably a screen formed of a metallic wire, such as aluminum. The polymeric resin is preferably a thermoplastic, such as HDPE, PVC, or polypropylene. The membrane, when installed as a liner for a liquid receptacle or a roof, has an exposed surface on the upper insulative layer. When so installed, the membrane is testable for pinhole openings by an electrical leak survey method, in which an electrical potential is applied between the scrim and a conductive probe. The probe is passed over the exposed surface, so that the electrical potential creates an electric spark between the probe and the scrim at the location of a pinhole opening. An RF signal is generated in response to the spark, and an alarm is actuated in response to the RF signal.

6 Claims, 2 Drawing Sheets

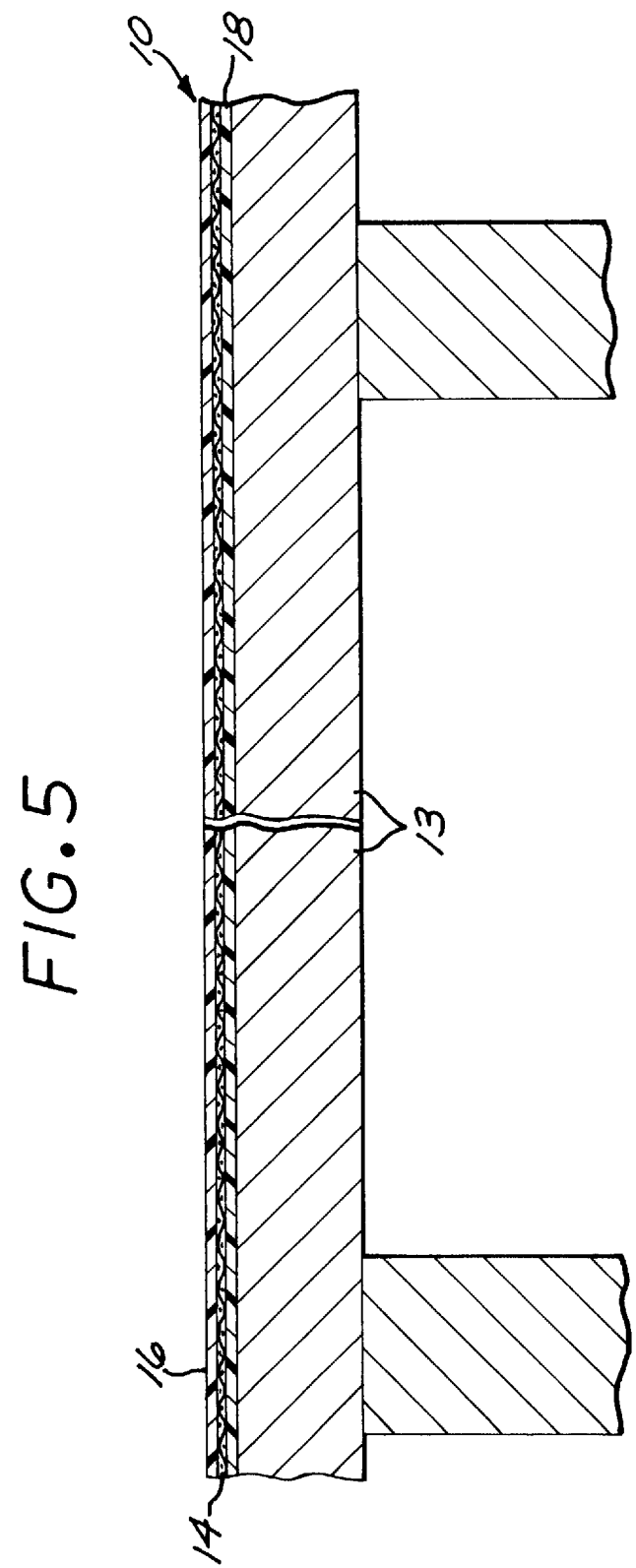

METHOD FOR DETECTING LEAKS IN A MEMBRANE

CROSS-REFERENCE TO RELATED APPLICATION

Not applicable

FEDERALLY FUNDED RESEARCH OR DEVELOPMENT

Not applicable

BACKGROUND OF THE INVENTION

The present invention relates generally to the field of moisture-impermeable membranes, such as those used as liners for roofing applications and for liquid containment areas, such as reservoirs and waste disposal sites. More specifically, it relates to a moisture-impermeable membrane for a roof, or for a containment area or receptacle, such as a reservoir, landfill, cistern, or the like, wherein the membrane provides an effective barrier against the seepage of the liquid through the roof or out of the containment area or receptacle. Still more specifically, the present invention relates to (a) a membrane of this type that provides a simple and effective mechanism for testing for pinhole openings that may permit leakage; and (b) a method of testing such a membrane for such openings.

It has been standard practice for some time to employ liquid-impermeable membranes as liners in liquid containment areas and receptacles to provide a substantially impermeable barrier between the contained liquid and the ground, thereby keeping the contained liquid from seeping out of the area or receptacle. Such membranes are especially useful for isolating any contaminants that may be in the contained liquid from groundwater. Such membranes have also been used in roofing applications, to provide an effective barrier against the seepage of rainwater and melted snow and ice through the roof into the interior of the building. These membranes are typically in the form of a sheet of thermoplastic material, such as high density polyethylene (HDPE), polyvinyl chloride (PVC), or polypropylene.

It is frequently necessary to test such membranes for pinhole openings, both upon installation, and periodically thereafter. Various "leak testing" devices and methods have been developed to find such openings. One method that has shown promise is the electrical survey method. This method requires the membrane to be in contact with a conductive layer. An electrical potential is established across the membrane or liner, and a conductive probe is then passed along the upper surface of the membrane. Pinhole openings are revealed by the detection of sparks between the probe and the membrane.

One way of implementing the electrical survey method is to glue or laminate a conductive foil to the bottom surface of the membrane. See, for example, U.S. Pat. No. 3,252,155—Surtees et al. One problem with this technique is that, due to different coefficients of thermal expansion between the foil and plastic layers, separation between them tends to occur over time. Furthermore, this laminated sheet material has proven difficult to install, is subject to possible corrosion, and is relatively expensive to manufacture.

Another system for electrical survey leak detection is disclosed in U.S. Pat. No. 5,288,168—Spencer. This patent discloses a sheet comprising upper and lower layers of plastic, with the lower layer being rendered electrically conductive by embedding conductive particles (such as carbon black) within it during fabrication. An electrical potential is established between the sheet and a conductive probe. The probe is then passed along the upper surface of the sheet. Pinhole openings are revealed by detecting sparks between the probe and the conductive layer.

One drawback to the system of the Spencer patent is that the addition of conductive particles to the sheet material has a detrimental effect on the physical characteristics of the liner. For example, the long-term durability of the membrane may be impaired, and its "weldability" may be reduced. ("Weldability" refers to the ability of the sheet to be joined to another sheet by a heat-sealed seam of high structural integrity.)

Another problem with prior art membranes is the need to provide good physical strength and structural integrity. To address this problem, it has been proposed to provide a laminated sheet structure, in which a polyester scrim is sandwiched between two layers of polymeric resin material, particularly thermoplastics such as HDPE, PVC, and polypropylene. This structure increases the tensile and tear strengths of the sheet.

The polyester scrim reinforcement has drawbacks, however. For example, if the sheet is punctured or cut, exposed polyester fibers from the scrim will absorb moisture, resulting in a wicking action that spreads the moisture throughout the scrim. This wicking phenomenon can cause delamination and a structural failure of the sheet. Another drawback to polyester scrim reinforcement is that in the lamination process, which is typically performed by heat sealing under pressure, the resin does not adhere well to the polyester scrim. The lamination bonding occurs only at the resin-to-resin contact areas between the polyester fibers, resulting in adhesion strengths on the order of only about 20 to 25 pounds per linear inch ("pli").

There has thus been a long-felt, but as yet unsatisfied, need for a strong, durable, "leak-testable" membrane that allows the use of the electrical leak survey method; that does not compromise the structural integrity of the membrane; and that provides good weldability characteristics. There is a further need for such a membrane that is economical to manufacture and easy to install, and that is not susceptible to failures due to, e.g., corrosion or separation between structural layers.

SUMMARY OF THE INVENTION

Broadly, the present invention is a "leak-testable" membrane, comprising a conductive scrim laminated between upper and lower layers of a durable insulative polymeric material. In a specific preferred embodiment, the scrim is a metal wire mesh screen, preferably of aluminum, and the polymeric material is a thermoplastic material, such as HDPE, PVC, or polypropylene.

In using the membrane of the present invention, the membrane is installed, by conventional installation means, to line a liquid containment receptacle or a roof. Electrical survey leak testing is performed by establishing an electrical potential between the scrim and a conductive probe. The probe is then passed along the upper surface of the membrane. The detection of sparks between the probe and the scrim reveals the presence of pinhole openings in the membrane.

The metallic scrim does not impair the structural integrity or durability of the membrane. In fact, the metallic scrim provides superior structural reinforcement, as compared to a polyester scrim. Unlike the polyester scrim construction, there is no wicking effect, and thus no moisture-induced separation between the polymeric layers. Furthermore, the polymer adheres well to the metallic scrim, resulting in lamination bonding not just at the polymer-to-polymer contact areas in the mesh openings, but also at the polymer-to-metal interfaces, resulting in adhesion strengths on the order of about 30 pli. Furthermore, as compared to polyester scrim, the metallic screen offers enhanced fire retardant qualities.

These and other benefits and advantages of the present invention will be more readily appreciated from the detailed description that follows.

BRIEF DESCRIPTION OF THE DRAWINGS

FIG. 5 is a cross-sectional view, similar to that of FIG. 2, showing a membrane in accordance with the present invention installed as a roof liner.

DETAILED DESCRIPTION OF A PREFERRED EMBODIMENT

Figure 1:
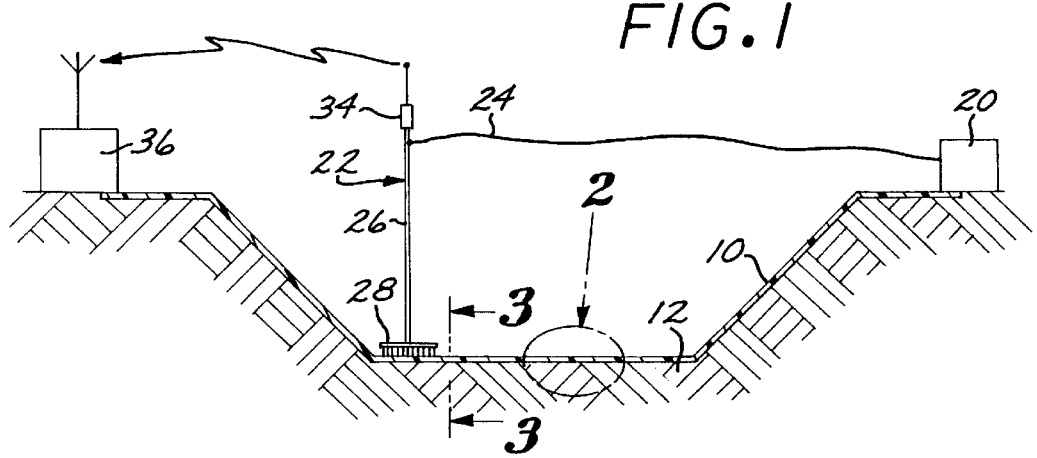
FIG. 1 is a cross-sectional view of a leak-testing system, employing a leak-testable membrane in accordance with the present invention installed as a liner in a liquid containment receptacle.

Referring now to the drawings, a leak-testable membrane 10, in accordance with a preferred embodiment of the present invention, is shown, in FIGS. 1 through 4, installed as a liner in a liquid containment receptacle 12. The receptacle 12 may be, for example, a hazardous waste disposal site, or a tank, canal, ditch, pond, or cistern for a polluted or contaminated liquid, or for potable water. In FIG. 5, the membrane 10 is shown installed on a liner on a roof 13.

Figure 2:
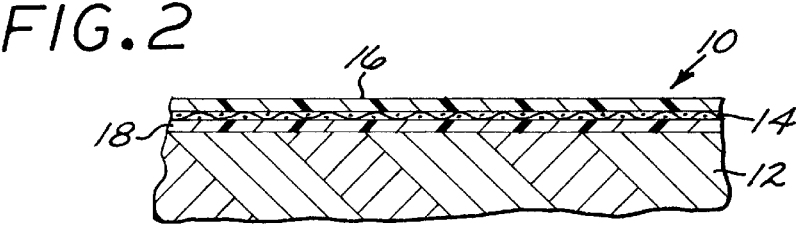
FIG. 2 is a detailed, enlarged cross-section view of the liner of FIG. 1, as contained within the area designated by the numeral 2 in FIG. 1.

As best shown in FIGS. 2 and 5, the membrane 10 is a laminated sheet, comprising a conductive mesh scrim 14, laminated between an upper polymeric resin layer 16 and a lower polymeric resin layer 18. The scrim 14 is preferably a metallic wire mesh screen, most preferably made of aluminum wire, although other metallic wires, and even carbon fibers, may provide good results. The polymeric resin layers 16, 18 are made of a durable, pliable, electrically-insulative, polymeric material that is impermeable to liquids and gas; that is easily formed into thin, strong sheets; and that has good "weldability" characteristics. A preferred material for the layers 16, 18 is a durable thermoplastic, such as HDPE, PVC, or polypropylene.

The lamination of the scrim 14 between the layers 16, 18 can be accomplished by any suitable method that is conventional in the art. A preferred lamination method includes the step of heat-sealing the layers 16, 18 together under pressure, with the scrim 14 between them. Under sufficient heat and pressure, the result is a bonding adhesion directly between the layers 16, 18 through the mesh openings in the scrim 14, as well as between each of the layers 16, 18 and the metal wires of which the scrim 14 is formed. The resultant structure yields enhanced tear and tensile strengths, and excellent resistance to delamination.

Figure 3:
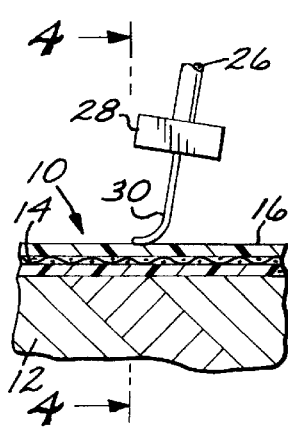
FIG. 3 is a cross-sectional view taken along line 3—3 of FIG. 1.
Figure 4:
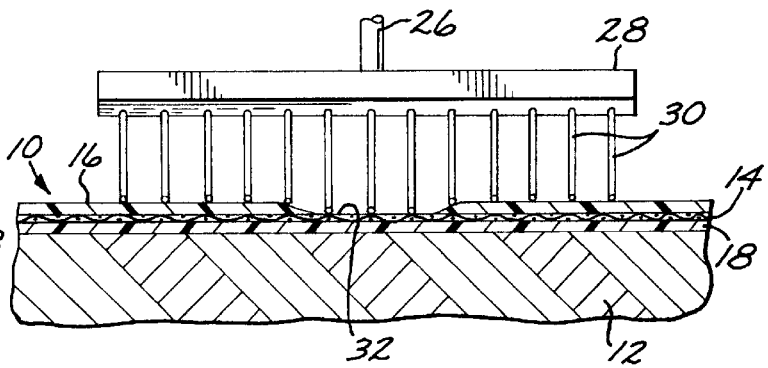
FIG. 4 is a cross-sectional view taken along line 4—4 of FIG. 3, showing the presence of a pinhole opening in the liner, the size of the opening being exaggerated for clarity.

FIGS. 1, 3, and 4 illustrate the method of using the membrane 10 in an electrical survey leak detection process.

As shown in FIG. 1, an electrical voltage source 20 applies an electrical potential between the scrim 14 and a spark discharge probe 22. The voltage source 20 is electrically connected to the scrim 14 by conventional means, such as terminals (not shown), and to the probe 22 by means of a cable 24. The applied potential is on the order of about 5,000 to 20,000 volts, preferably about 10,000 to 15,000 volts. The magnitude of the optimum applied potential will depend on the resistivity and the thickness of the upper polymeric resin layer 16.

The probe 22 is advantageously of the type described in U.S. Pat. No. 5,288,168—Spencer. Specifically, the probe 22 comprises an elongate insulative handle 26 having a brush-like head 28 attached to its lower end. The head 28 includes a plurality of metal wire bristles 30, preferably of brass, that are electrically connected to the voltage source 20 via the cable 24.

When the membrane 10 is installed as a liner for a receptacle or a roof, as shown in the drawings, the upper polymeric resin layer 16 has an exposed upper surface. The brush head 28 of the probe 22 is pushed along the exposed surface of the upper polymeric resin layer 16, whereby the ends of the bristles 30 are brought into contact with that surface. When a pinhole opening 32 is encountered (FIG. 4), the conductive wire of the scrim 14 is exposed to the ends of the bristles 30, and a spark is created between the bristles 30 and the scrim 14, due to the high electrical potential created between them. This spark is detected by conventional spark detection means, well-known in the art. For example, the spark can be detected by a spark detection circuit module 34 mounted on the probe 22. The spark detection circuit module 34 generates an RF signal indicative of the occurrence of a spark, and this signal is then transmitted to a receiver 36 that generates an audible and/or visible alarm (not shown). The spark detection circuit module 34 may advantageously include circuitry (not shown) that encodes the RF signal with a value that indicates the location of the pinhole opening 32, and the receiver 36 would then include complementary circuitry (not shown) that would decode the signal to provide a visual display of the locations of detected pinhole openings. The design and construction of the circuitry in the module 34 and receiver 36 to perform the foregoing functions are well within the ordinary level of skill in the pertinent arts.

Spark detection systems that include a high voltage source 20 for establishing the required potential between the probe 22 and the scrim 14 are commercially available. One such spark detection system that may be used is the Pipeline Inspection Co. Model 725.

The present invention thus provides a fluid-impermeable liner that can be economically manufactured, easily installed, and easily and efficiently tested for pinhole openings. Furthermore, the present invention provides a liner that exhibits good structural integrity and durability. In addition, the present invention provides an efficient, reliable, and economical method for detecting pinhole openings in fluid-impermeable liners.

While a preferred embodiment of the invention has been described above and shown in the drawings, a number of variations and modifications may suggest themselves to those skilled in the pertinent arts. For example, the conductive scrim 14 can be made of any metallic wire or conductive fiber that has suitable electrical conductivity and adhesion with the polymeric resin layers 16, 18. Also, the probe 22 may assume any of a variety of forms that may be adapted to the specific application involved and the needs of the user.

These and other variations and modifications are considered to be within the spirit and scope of the present invention, as defined in the claims that follow.

What is claimed is:

1. A method of detecting pinhole openings in a fluid impermeable membrane, comprising the steps of:

(a) providing a membrane comprising a conductive mesh scrim laminated between an upper polymeric resin layer and a lower polymeric resin layer, the upper layer having an exposed upper surface;

(b) providing a conductive probe;

(c) applying an electrical potential between the probe and the scrim;

(d) passing the probe along the exposed upper surface of the upper layer; and (e) detecting an electrical spark between the probe and the scrim.

2. The method of claim 1, further comprising the steps of:

(f) generating an RF signal in response to the detection of a spark; and (g) actuating an alarm in response to the RF signal.

3. The method of claim 1, wherein the step of applying the electrical potential comprises the step of applying an electrical potential of between about 5000V and about 20,000V.

4. The method of claim 2, wherein the step of applying the electrical potential comprises the step of applying an electrical potential of between about 5000V and about 20,000V.

5. The method of claim 3, wherein the step of applying the electrical potential comprises the step of applying an electrical potential of between about 10,000V and about 15,000V.

6. The method of claim 4, wherein the step of applying the electrical potential comprises the step of applying an electrical potential of between about 10,000V and about 15,000V.

* * * * *